(12) United States Patent
Eckermann et al.

(10) Patent No.: US 8,721,989 B2
(45) Date of Patent: May 13, 2014

(54) APPARATUS FOR MEASURING BLOOD OXYGEN SATURATION

(75) Inventors: Martin Eckermann, Rostock (DE); Thomas Scholl, Wismar (DE)

(73) Assignee: EnviteC-Wismar GmbH, Wismar (DE)

( * ) Notice: Subject to any disclaimer, the term of this patent is extended or adjusted under 35 U.S.C. 154(b) by 251 days.

(21) Appl. No.: 12/742,145

(22) PCT Filed: Nov. 7, 2008

(86) PCT No.: PCT/EP2008/009429
§ 371 (c)(1),
(2), (4) Date: Jun. 1, 2010

(87) PCT Pub. No.: WO2009/019044
PCT Pub. Date: Feb. 12, 2009

(65) Prior Publication Data
US 2010/0279335 A1    Nov. 4, 2010

(30) Foreign Application Priority Data

Nov. 9, 2007   (DE) .......................... 10 2007 053 599

(51) Int. Cl.
*G01N 33/00* (2006.01)
(52) U.S. Cl.
USPC .................. 422/404; 422/401; 422/82.05
(58) Field of Classification Search
USPC ....................... 422/404, 401, 82.05
See application file for complete search history.

(56) References Cited

U.S. PATENT DOCUMENTS

| | | |
|---|---|---|
| 3,017,885 A | 1/1962 | Robicsek |
| 5,701,155 A | 12/1997 | Wood |
| 5,776,059 A | 7/1998 | Kaestle et al. |
| 6,154,667 A | 11/2000 | Miura et al. |
| 2007/0027375 A1 | 2/2007 | Melker |
| 2008/0297764 A1 | 12/2008 | Schöller et al. |

FOREIGN PATENT DOCUMENTS

| | | |
|---|---|---|
| DE | 91 02 784 U1 | 7/1991 |
| DE | 37 03 458 C2 | 8/1991 |
| DE | 10 2006 034 843 | 2/2007 |
| DE | 10 2005 053623 A1 | 5/2007 |
| DE | 10 2008 017 403 | 10/2009 |
| EP | 0 227 401 A | 7/1987 |
| EP | 0 619 981 A1 | 10/1994 |
| EP | 1 257 190 B1 | 4/2006 |
| EP | 2 063 772 B1 | 8/2011 |
| GB | 2 320 566 A | 6/1998 |
| JP | 2004-187920 | 7/2008 |

(Continued)

OTHER PUBLICATIONS

Hewlett Packard Journal "A New Family of Sensors for Pulse Oximetry", vol. 48(1), pp. 39-53 (Feb. 1997).

(Continued)

*Primary Examiner* — Sam P Siefke
(74) *Attorney, Agent, or Firm* — Chalin Smith; Smith Patent

(57) ABSTRACT

The invention relates to an apparatus for measuring blood oxygen saturation, comprising a housing (1), a sensor (2), a connecting cable (3) and a plug (4), wherein the housing (1) has a cavity (5) for accepting a patient's tissue which is supplied with blood;

the sensor (2) which is arranged on the housing and has at least one light source (21) for the emission of light which passes through the tissue which is supplied with blood and a detector (22) for receiving the light passing through the tissue which is supplied with blood; and the apparatus can be connected to an evaluation unit via the plug (4).

15 Claims, 3 Drawing Sheets

(56) References Cited

FOREIGN PATENT DOCUMENTS

| WO | WO 00/061000 | 10/2000 |
|---|---|---|
| WO | WO 2005/065540 | 7/2005 |
| WO | WO 2007/019420 | 2/2007 |

OTHER PUBLICATIONS

Hewlett Packard GmbH, "M1190A, M1191A, M1192A, M1193A, M1194A, M1195A Pulse Oximetry Transducers" (1998).

Food and Drug Administration, Aktenzeichen K032979, 510(k) Summary of the Phillips Reusuable $SpO_2$ Sensors M1191T, M1192T and M1193T (Feb. 2004).

Food and Drug Administration, Aktenzeichen K063783, 510(k) Summary of the Phillips Reusuable $SpO_2$ Sensors M1191T, M1192T and M1193T (Apr. 2007).

Philips Medical Systems "$SpO_2$ Sensor Compatibility Sheet" for $SpO_2$ Sensors M1191T, M1192T, M1193T, M1131A, M1132A, and M1133A (2007).

Philips Medical Systems "Reusable $SpO_2$ T-Series Sensors: Instructions For Use" for $SpO_2$ Sensors M1191T, M1192T and M1193T, pp. 19-27 (Jan. 2005).

Philips Medical Systems "Reusable $SpO_2$ Sensors" (Jan. 2005).

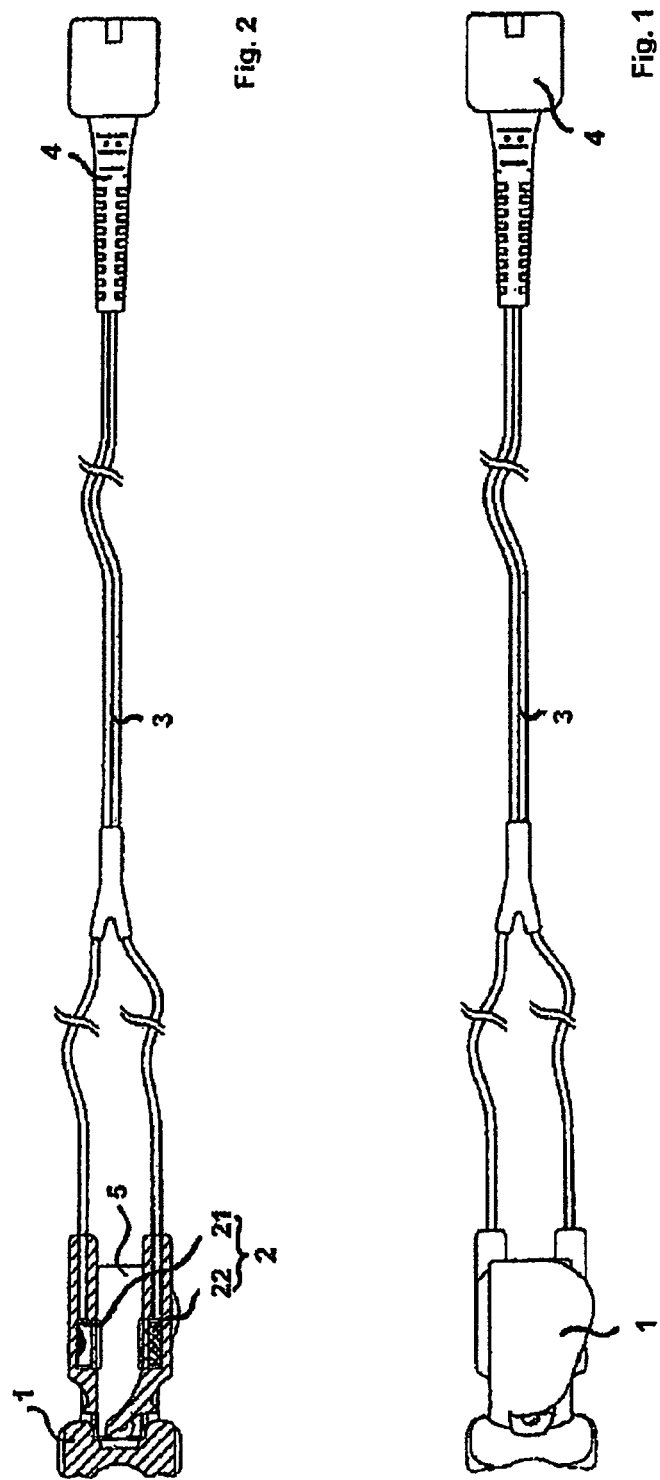

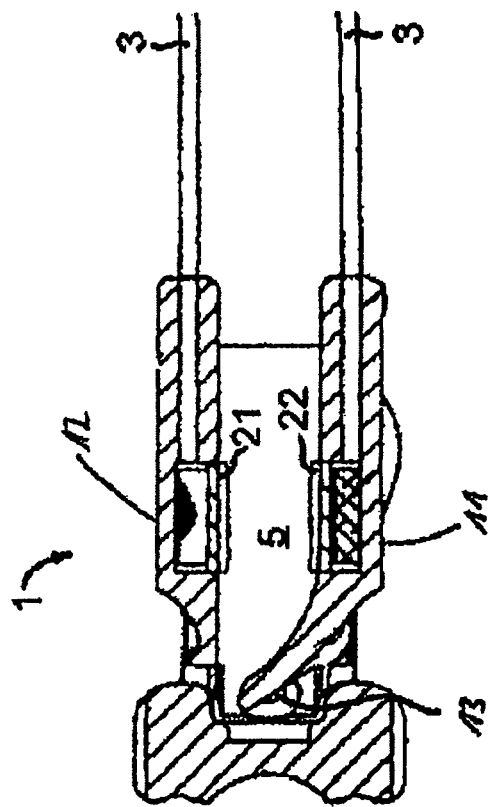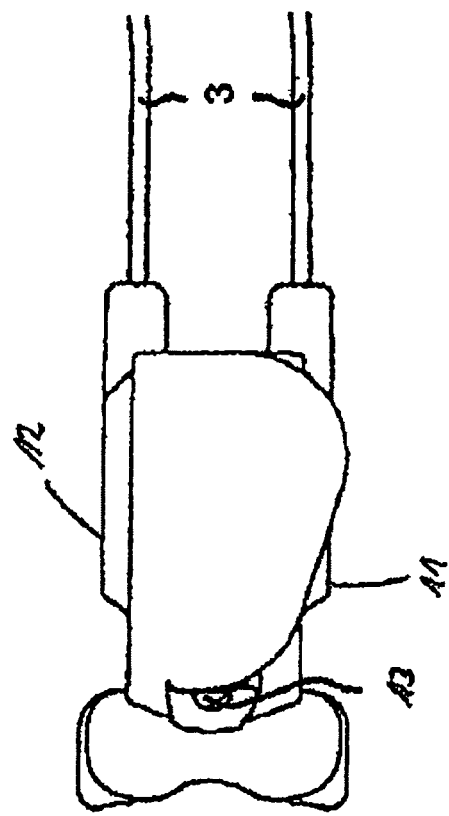
Fig. 4
Fig. 3

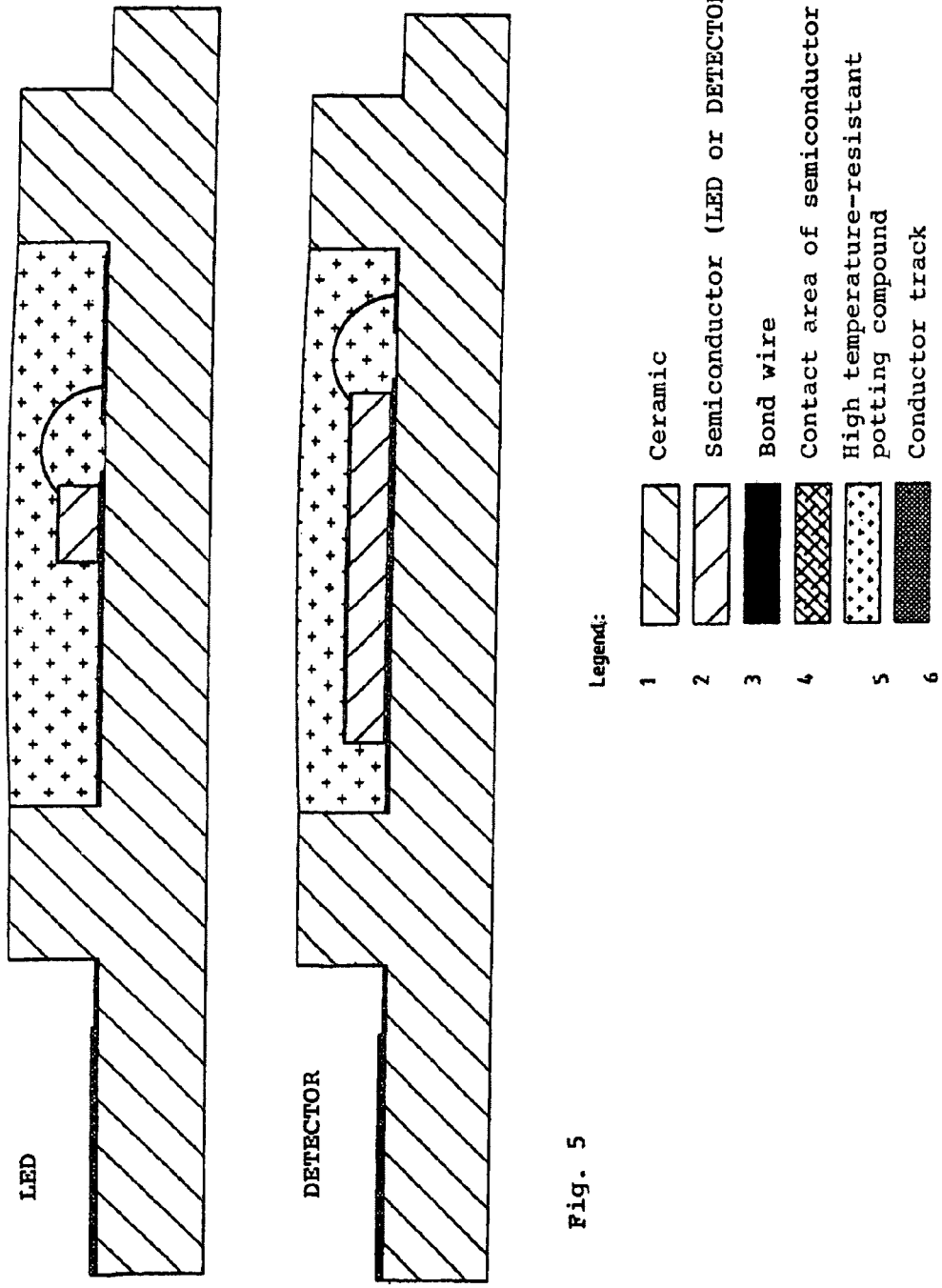

APPARATUS FOR MEASURING BLOOD OXYGEN SATURATION

This application corresponds to the national phase of International Application No. PCT/EP2008/09429 filed Nov. 7, 2008, which, in turn, claims priority to German Application No. 10 2007 053 599.8 filed Nov. 9, 2007, the contents of which are incorporated by reference herein in their entirety.

The invention relates to an apparatus for measuring blood oxygen saturation. It furthermore relates to a method for producing such an apparatus and uses of the apparatus.

The measurement of blood oxygen saturation is a method widely used in medicine, such a measurement being carried out in the majority of cases non-invasively by means of a pulse oximeter. A pulse oximeter consists as a rule of a clip-like housing having a cavity into which, for example, the finger, a toe, the ear lobe or another tissue of a person which is supplied with blood can be inserted. Present in the surface of the cavity is a light source which is opposite a detector which is likewise present in the surface of the cavity, in such a way that the tissue which is supplied with blood is present between the light source and the detector. The light source, usually an LED, omits only light having two different wavelengths, for example 660 nm and 940 nm. The tissue which is supplied with blood and through which the light passes absorbs a part of the light, the light transmittance being inversely proportional to the concentration of haemoglobin. The light source and the detector form the pulse oximeter element which is designated as a sensor. A corresponding apparatus is described, for example in EP-A-1 168 959.

The detector, usually a photodetector, receives the transmitted light and converts it into electrical signals. The electrical signals are transported by means of electrical conductors which are formed in the housing via a connecting cable to an evaluation unit. For this purpose, the cable has a plug which can be inserted into a corresponding connecting element in the evaluation unit so that an electrical connection is produced between the detector and the evaluation unit. On the other hand, electrical conductors for the power supply of the light source and of the detector are led through the cable.

It is standard medical practice regularly to sterilize medical devices in order as substantially as possible to ensure freedom of the devices from germs. It is now usual to carry out the sterilization by means of autoclaving. For this purpose, the device to be sterilized is introduced into an autoclave and exposed there to saturated steam typically for about 2 to 20 min or even longer at a temperature of 115° to 140° C. and a pressure of about 2 bar.

Medical devices consist as a rule of a plurality of individual elements which are coupled in multiple and different ways, such as mechanically, electrically or optically, magnetically, etc and/or combinations thereof and have an operative connection to one another in order to realize certain functions. Connections which can be mechanically disconnected are required in particular in order to be able to uncouple elements of the medical device which are not sterilizable and to be able to subject them to a sterilization process other than autoclaving. Accordingly, DE 91 02 784 U1 proposes coupling elements with the aid of which a temperature sensor can be disconnected from the connecting cable, permitting autoclaving of the temperature sensor. The connecting cable itself is either not sterilized or subjected to a simple sterilization by wiping.

For sufficiently safe sterilization of the pulse oximeter described above, the connecting cable must therefore first be disconnected from the evaluation unit by pulling the plug out of the connecting unit of the evaluation device. The housing, the sensor comprising the light source and the detector, the connecting cable and the plug, which are connected to one another in an interlocking manner, and the actual measuring device for determining the blood oxygen saturation are then separated from one another so that four individual elements are obtained: housing, sensor, cable and plug. The dismantling into these individual elements is necessary since certain individual elements (such as, for example, the connecting the cable and the sensor) cannot be subjected to autoclaving or at least require to be sheathed with a hollow body which consists of a plastic resistant to high temperatures. The hollow body is intended to prevent damage to the individual element by overheating during the autoclaving. If the individual element cannot be autoclaved, another sterilization method must be used.

In addition, conventional apparatuses for measuring the blood oxygen saturation cannot be autoclaved as one piece since, owing to the high pressure of about 2 bar, steam can easily penetrate into the electronic components and damage the apparatus thereby. A further problem is that the required optical semiconductor components, which as a rule comprise an LED as a sensor and a Si photodiode as a receiver, are often not sufficiently temperature resistant to withstand the high temperatures during autoclaving. The person skilled in the art was therefore prevented from providing integral apparatuses of said type.

The dismantling of the measuring device into its four individual elements is, however, associated with several disadvantages. It is firstly time-consuming since on the one hand dismantling and the assembly of the measuring device are required and on the other hand individual parts must be subjected to different sterilization methods, for which appropriate apparatuses are required. Secondly, it is susceptible to errors since firstly errors may be made during the assembly of the individual elements and secondly sterilized and non-sterilized individual elements may be united.

An object of the invention is therefore to overcome the disadvantages of the apparatuses according to the prior art. It is intended in particular to provide an apparatus for measuring blood oxygen saturation which permits sterilization without dismantling of the apparatus into its individual parts being required. Furthermore, it is intended to provide a method for producing such an apparatus and uses of the apparatus.

This object is achieved by the features of claims 1, 11 and 13. Expedient configurations of the invention are evident from the features of claims 2 to 10, 12, 14 and 15.

The invention provides an apparatus for measuring blood oxygen saturation which comprises a housing, a sensor, a connecting cable and a plug, wherein
  the housing has a cavity for accepting the patient's tissue which is supplied with blood;
  the sensor which is arranged on the housing and has at least one light source for the emission of light, which passes through the tissue which is supplied with blood, and a detector for receiving the light passing through the tissue which is supplied with blood; and
  the apparatus can be connected to an evaluation unit via the plug;
  the housing, the sensor, the connecting cable and the plug are connected to one another in an interlocking and nondetachable manner; and
  the outsides of at least the housing, the connecting cable and the plug are formed from a first flexible, autoclavable material.

The apparatus according to the invention can be sterilized in an autoclave without dismantling into its individual elements since the connecting cable and the plug can be autoclaved owing to the flexible, autoclavable material which forms its outside. By means of the measures described below, it is moreover possible to provide housing and sensor so that the sensor, too, can be autoclaved without damage. Assembly of the individual elements after the sterilization is thus likewise no longer required. Moreover, errors in the dismantling or assembly and in the separate sterilization of the individual elements are avoided.

The apparatus according to the invention permits sterilization in a single process step, which considerably simplifies the handling of the apparatus and accelerates the sterilization. Time-consuming preprocessing and subsequent processing of the apparatus in association with the autoclaving are not required, which means a further time gain.

The term "outside" is understood in the present invention as meaning any surface which comes into contact with the environment and may thus be contaminated with biological germs. Surfaces which are not exposed to the environment, for example the inner surface of the closed housing or that side of the insulation material of the connecting cable which faces the electrical conductors of connecting cable, should not be regarded as the outside, but the housing, the insulation material of the connecting cable and the housing of the plug may be formed completely from the flexible, autoclavable material. The electrical contacts of the plug, which are formed from electrically conductive metal, which can be engaged by the electrical contacts of the connecting element with the evaluation device, have no outsides comprising the first flexible, autoclavable material but are exposed since they in any case consist of an autoclavable material, a metal.

The term "autoclavable material" is understood as meaning a material which is not changed by sterilization in the autoclave with regard to its chemical and physical properties. The autoclavable material should therefore be heat-resistant at temperatures up to 180° C. and should not change, for example dissolve or decompose, under the action of saturated steam.

The "flexible material" is understood as meaning a resilient material which, after deformation under the action of a force, returns to its original state after elimination of the force. Preferred flexible materials are elastomeric materials.

The flexible, autoclavable material is preferably a plastic, more preferably an elastomer, particularly preferably a silicone.

In an embodiment of the invention, the housing, the connecting cable and/or the plug have a coating comprising the first flexible, autoclavable material, this coating forming in each case the outside of the housing, of the connecting cable and/or of the plug.

Preferably, the outsides of the sensor consist of a second autoclavable material, it being possible for the second autoclavable material to be the same as the first flexible, autoclavable material or to be a material other than the first flexible, autoclavable material. The second autoclavable material must be transparent to the light emitted by the sensor. Preferably, the second autoclavable material is likewise a flexible, autoclavable material.

Since the sensor system of the sensor is as a rule heat-sensitive, the sensor system is usually in any case enclosed by a material which is itself autoclavable or has an autoclavable coating, for example in the form of a covering. Alternatively, the sensor can be integrated into the housing so that the outsides of the sensor which face the tissue which is supplied with blood are formed by the housing. In this case, the first flexible autoclavable material must be transparent to the emitted light.

In a preferred embodiment, the housing, the connecting cable, the plug and optionally the sensor are completely enclosed in a common covering comprising the first flexible autoclavable material. The first flexible autoclavable material forms a sheath for the housing, the sensor, the connecting cable and the plug.

Such a sheath can also be produced subsequently in the case of existing apparatuses which consist of the individual elements comprising housing, sensor, connecting cable and plug.

It was moreover surprisingly found that the known problems due to the poor temperature resistance of optical semiconductor components can be solved by the targeted choice of components stable to high temperatures. For this purpose, for example, components which have the required temperature stability can be chosen from a conventional batch of corresponding components.

In addition, it has proved to be advantageous if transmitter/light source and receiver/detector are mounted on a ceramic support and enclosed with an autoclavable material transparent to the emitted light, preferably embedded therein. As a result, the resistance to the superheated steam and the high pressure is improved.

For example, the contact areas (conductor tracks) can be applied with a temperature-resistant adhesive to a ceramic body. The undersides of the semiconductor components can then be mounted on the conductor track using a temperature-resistant conductive adhesive. Thereafter, contact is established between the top of the semiconductor components and the second conductor track by means of a bond wire, and the semiconductor components and the bond wire are completely encapsulated with a transparent, temperature- and pressure-stable, steam-resistant potting material.

In the case of the specific, above-described structure of sensor and receiver, it should be ensured that the transparent potting material is sufficiently temperature-resistant. The high temperature during autoclaving otherwise leads to discolourations or opacity of the potting material. The opacity of the material would lead to a decisive deterioration or even to complete failure of the sensor properties. Moreover, when choosing all materials used, it should be ensured that they have similar coefficients of thermal expansion, at least in the contact areas, in order to prevent the elements from becoming detached from one another at high temperatures. Particularly in the case of the semiconductor detector, the coefficients of thermal expansion play a decisive role since said detector has a large contact area of 3-8 $mm^2$ with the conductor track.

The known problems in the autoclaving of the sensors in apparatuses for measuring blood oxygen saturation can therefore be overcome, according to the invention, by three measures, which can be used individually or in any desired combination with one another. Firstly, light source and detector can be mounted on a ceramic support in order thus to increase the temperature and pressure stability. Secondly, light source and detector, including their support, preferably the ceramic support, can be encapsulated with a transparent potting material. Thirdly, it is advantageous to choose the materials used for the construction of light source and detector so that they have differences which are as small as possible in their coefficients of thermal expansion.

Furthermore, the housing is advantageously a silicone housing having injection-moulded transparent silicone windows under which light source and sensor are arranged. Transparent silicone windows are understood as meaning those windows which are transparent to the emitted light. By injection-moulding the silicone windows in the silicone housing, particular protection of the electronic components from the superheated steam is ensured, even at high temperatures.

Finally, it has proved to be advantageous if the plug is injection-moulded onto the connecting cable, preferably with a suitable temperature-resistant material.

Furthermore, the invention envisages a method which comprises
- the provision of a housing, a sensor, a connecting cable and a plug, at least one of these parts having an outside comprising a non-heat-resistant material; and
- the spraying of the outsides of the parts with an autoclavable substance;
- the autoclavable substance having a gel- or foam-like consistency or being present in the gaseous state so that the autoclavable substance diffuses into the surfaces of the parts with formation of the outsides comprising the first flexible, autoclavable material.

The autoclavable substance which, after application to the parts of the apparatus, represents the outsides comprising flexible, autoclavable material thus forms a coating on all parts of the apparatus. The coating consists of the first flexible, autoclavable material. This coating comprising the first flexible, autoclavable material preferably represents a sheathing of the entire apparatus.

The first flexible autoclavable material can be used as the autoclavable substance. However, it is also possible for the autoclavable substance to form the flexible autoclavable material only after application to the parts of the apparatus.

The term "parts" relates to the housing, the sensor, the connecting cable and the plug of the apparatus. The parts are connected to one another in an interlocking manner. After application of the autoclavable substance, the parts can no longer separated from one another to give individual elements.

The apparatus according to the invention is advantageously used for measuring blood oxygen saturation, in particular the $S_pO_2$ value. It is suitable in particular for continuous monitoring of the oxygen saturation.

The invention is explained in more detail below on the basis of an example with reference to the drawings. There, FIG. 1 shows a plan view of an embodiment of the apparatus according to the invention;

FIG. 2 shows a sectional view of the embodiment shown in FIG. 1;

FIG. 3 shows a detailed view of the housing of the first embodiment, which housing is shown in FIG. 1;

FIG. 4 shows a detailed view of the housing of the first embodiment, which housing is shown in FIG. 2;

FIG. 5 shows schematic structures of a preferred light source (LED) and a preferred detector.

According to FIGS. 1 and 2, the apparatus according to the invention has a housing 1, a sensor 2, a connecting cable 3 and a plug 4. In the housing 1, the sensor 2, which comprises a light source 21 and a detector 22, is arranged in such a way that light which is emitted by the light source 21 is received by the detector 22 after transmission by a patient's tissue which is supplied with blood.

The housing 1 is connected in an interlocking manner to a first end of the connecting cable 3, the second end of the connecting cable 3 being connected in an interlocking manner to the plug 4. Running in the connecting cable 3 are the electrical conductors (not shown) which connect the light source 21 and the detector 22 of the sensor 2 in the housing 1 to the pins of the plug 4, which can be inserted into corresponding electrical contacts of a connecting element of the evaluation unit (not shown).

The housing 1, the sensor 2, the connecting cable 3 and the plug 4 are coated on their outsides with silicone so that all parts of the apparatus are covered with a flexible, autoclavable material. In particular, the cavity 5 of the housing 1 into which the patient's tissue which is supplied with blood is inserted is also covered by the flexible, autoclavable material.

According to FIGS. 3 and 4, the housing 1 has, by way of example, a base plate 11 and a cover plate 12 which is a distance away from the base plate 11 and is rotatable in a plane which is parallel to the base plate 11. A section of the base plate 11 is in the form of a support for the tissue which is supplied with blood, for example a finger. A first side element and a second side element are arranged on the longitudinal sides of the base plate 11, while a third side element is arranged on the narrow side of the base plate 11. The side elements extend perpendicularly to the base plate 11 up to the cover plate 12. The side elements together with the base plate 11 and the cover plate 12 bound the cavity 5 for accepting the tissue which is supplied with blood, the cavity 5 being closed at the bottom by the base plate 11 and at the top by the cover plate 12. Between the narrow sides of the base plate 11 and cover plate 12, which face away from the third side element, the cavity 5 is open to the environment.

The base plate 11 and the cover plate 12 each have an anti-kink device for the cable 3.

Furthermore, the housing has a spring element 13 which is fastened to the third side element and to the base plate 11 on the other hand. The spring element 13 clamps the base plate 11 in the direction of the cover plate 12. Owing to the spring force, the housing 1 can be detachably fastened in the manner of a clip to the tissue which is supplied with blood.

The light source 21 of the sensor 2 is arranged on the outside of the cover plate 12, which faces the base plate 11, while the detector 22 is arranged on the outside of the base plate 11, which faces the cover plate 12. Light source 21 and detector 22 are therefore opposite one another.

The outsides of the housing 1 which are in contact with the environment are coated with a flexible, autoclavable material. Specifically, these are the base plate 11, the cover plate 12 and the side elements. Likewise, the spring element 13 is coated with the flexible, autoclavable material if it is not completely enclosed by the housing 1 and therefore exposed to the environment.

Alternatively, all elements of the housing, i.e. the base plate 11, the cover plate 12, the side elements and the spring element 13, can be formed completely from the flexible, autoclavable material.

The invention claimed is:

1. An apparatus for measuring blood oxygen saturation comprising a housing (1), a sensor (2), a connecting cable (3) and a plug (4), wherein:
- the housing (1) has a cavity (5) for accepting a patient's tissue that is supplied with blood;
- the housing (1), sensor (2), connecting cable (3) and plug (4) comprise exposed exterior surfaces and enclosed interior surfaces;
- the sensor (2) is arranged on the housing and has at least one light source (21) for the emission of light that passes through said patient tissue and a detector (22) for receiving the light passing through said patient tissue; and
- the apparatus can be connected to an evaluation unit via the plug (4);

further wherein:
- the housing (1), the sensor (2), the connecting cable (3) and the plug (4) are connected to one another in an interlocking and nondetachable manner; and the exterior surfaces of at least the housing (1), the connecting cable (3) and the plug (4) are formed of a first flexible, autoclavable material that is heat resistant at temperatures up to 180°C. and that has chemical and physical properties that remain unchanged during sterilization by autoclave; and the light source (21) and the detector (22) have a temperature stability sufficient to withstand high temperatures that accompany autoclaving.

2. The apparatus according to claim 1, characterized in that the entirety of the housing (1) is formed of the first flexible, autoclavable material.

3. The apparatus according to claim 1, characterized in that the exterior surface of the housing (1) comprises a coating comprising the first flexible, autoclavable material.

4. The apparatus according to claim 1, characterized in that the exterior surface of the sensor (2) consists of a second autoclavable material, wherein the second autoclavable material is either the same as the first flexible, autoclavable material or a material other than the first flexible, autoclavable material.

5. The apparatus according to claim 1, characterized in that the exterior surface of the connecting cable (3) comprises an insulation comprising the first flexible, autoclavable material.

6. The apparatus according to claim 1, characterized in that the sensor (2) is integrated into the housing (1) and the exterior surface of the sensor (2) that faces said patient tissue is formed by the housing.

7. The apparatus according to claim 1, characterized in that the housing (1) has a base plate (11) and a cover plate (12) that is a distance away from the base plate (11) and is rotatable in a plane that is parallel to the base plate (11), wherein:
a first side element (13) and a second side element (14) are arranged on the longitudinal sides of the base plate (11) while a third side element is arranged on the narrow side of the base plate (11);
the side elements extend perpendicularly to the base plate (11) up to the cover plate (12) and, together with the base plate (11) and the cover plate (12), bound the cavity (5) for accepting said patient tissue, the cavity (5) being closed at the bottom by the base plate (11) and at the top by the cover plate (12); and
the housing (1) has a spring element (13) that is fastened to the third side element and to the base plate (11) on the other hand, the spring element (13) clamping the base plate (11) in the direction of the cover plate (12).

8. The apparatus according to claim 7, characterized in that the light source (21) of the sensor (2) is arranged on the outside of the cover plate (12), which faces the base plate (11), and the detector (22) is arranged on the outside of the base plate (11) which faces the cover plate (12).

9. The apparatus according to claim 1, characterized in that the first flexible, autoclavable material is a silicone.

10. The apparatus according to claim 4, characterized in that the second autoclavable material is a silicone.

11. A method for producing an apparatus comprising a housing (1), a sensor (2), a connecting cable (3), and a plug (4) wherein:
the housing (1) has a cavity (5) for accepting a patient's tissue that is supplied with blood;
the housing (1), sensor (2), connecting cable (3) and plug (4) compose exposed exterior surfaces and enclosed interior surfaces;
the sensor (2) is arranged on the housing and has at least one light source (21) for the emission of light that passes through said pattern tissue and a detector (22) for receiving the light passing through said patient tissue; and the apparatus can be connected to an evaluation unit via the plug (4);
further wherein:
the housing (1), the sensor (2), the connecting cable (3) and the plug (4) are connected to one another in an interlocking and nondetachable manner; and
the exterior surfaces of at least the housing (1), the connecting cable (3) and the plug (4) are formed of a first flexible, autoclavable material that is heat resistant at temperatures up to 180° C. and that has chemical and physical properties that remain unchanged during sterilization by autoclave; and
the light source (21) and the detector (22) have a temperature stability sufficient to withstand high temperatures that accompany autoclaving;
wherein said method comprises the steps of:
providing a housing (1), a sensor (2), a connecting cable (3) and a plug (4), wherein at least one of these parts has an exterior formed of a non-autoclavable material;
spraying of the exterior of these pans with an autoclavable substance, said autoclavable substance having a gel- or foam-like consistency or being present in the gaseous slate so that the flexible, autoclavable substance diffuses into the surfaces of the parts with formation of the outsides comprising a flexible, autoclavable material.

12. The method according to claim 11, characterized in that the autoclavable substance forms a coating comprising a flexible, autoclavable material.

13. A method of measuring blood oxygen saturation in a patient's tissue that is supplied with blood using an apparatus comprising a housing (1). a sensor (2), a connecting cable (3). and a plug (4) wherein
the housing (1) has a cavity (5) for accepting a patient's tissue that is supplied with blood,
the housing (I), sensor (2). connecting cable (3) and plug (4) comprise exposed exterior surfaces and enclosed interior surfaces;
the sensor (2) is arranged on the housing and has at least one light source (21) for the emission of light that passes through said patient tissue and a detector (22) for receiving the light passing through said patient tissue, and the apparatus can be connected to an evaluation unit via the plug (4);
further wherein
the housing (1), the sensor (2), the connecting cable (3) and the plug (4) arc connected to one another in an interlocking and nondetachable manner, and
the exterior surfaces of at least the housing (1). the connecting cable (3) and the plug (4) are formed of a first flexible, autoclavable material that is heal resistant at temperatures up to 180° C. and that has chemical and physical properties that remain unchanged during sterilisation by autoclave; and
the light source (21) and the detector (22) have a temperature stability sufficient to withstand high temperatures that accompany autoclaving;
wherein, said method comprises the steps of:
placing said patient tissue in the cavity (5) of the housing (I);
passing light through said patient tissue.
detecting the light passed through said patient tissue.

14. The method according to claim 13, further comprising the step of using the apparatus according to claim I to measure the oxygen saturation $S_pO_2$ of said patient tissue.

15. The method according to claim 13, further comprising the step of using the apparatus according to claim 1 to monitor the oxygen saturation of said patient tissue.

* * * * *

UNITED STATES PATENT AND TRADEMARK OFFICE
CERTIFICATE OF CORRECTION

PATENT NO.        : 8,721,989 B2
APPLICATION NO.   : 12/742145
DATED             : May 13, 2014
INVENTOR(S)       : Martin Eckermann et al.

Page 1 of 1

It is certified that error appears in the above-identified patent and that said Letters Patent is hereby corrected as shown below:

In the Claims

In claim 11, at column 7, line 62, replace the word "compose" with -- comprise --.

In claim 11, at column 8, line 21, replace the word "pans" with -- parts --.

In claim 11, at column 8, line 24, replace the word "slate" with -- state --.

In claim 13, at column 8, line 49, replace the word "arc" with -- are --.

In claim 13, at column 8, line 53, replace the word "heal" with -- heat --.

In claim 13, at column 8, lines 55-57, replace the word "sterilisation" with -- sterilization --.

Signed and Sealed this
Fifth Day of August, 2014

Michelle K. Lee
*Deputy Director of the United States Patent and Trademark Office*